US011457837B2

United States Patent
Wu (10) Patent No.: US 11,457,837 B2
(45) Date of Patent: Oct. 4, 2022

(54) DIRECTION CONTROL APPARATUS WITH SENSOR, AND METHOD AND SYSTEM FOR DETERMINING DRIVER STATUS USING THE SAME

(71) Applicant: PIXART IMAGING INC., Hsin-Chu (TW)

(72) Inventor: Sung-Han Wu, Hsin-Chu (TW)

(73) Assignee: PIXART IMAGING INC., Hsin-Chu (TW)

( * ) Notice: Subject to any disclaimer, the term of this patent is extended or adjusted under 35 U.S.C. 154(b) by 840 days.

(21) Appl. No.: 16/386,318

(22) Filed: Apr. 17, 2019

(65) Prior Publication Data

US 2019/0241191 A1 Aug. 8, 2019

Related U.S. Application Data

(63) Continuation-in-part of application No. 15/689,293, filed on Aug. 29, 2017, now Pat. No. 10,603,566.

(30) Foreign Application Priority Data

Aug. 6, 2018 (CN) .......................... 201810884287.7

(51) Int. Cl.
   *A61B 5/18* (2006.01)
   *A61B 5/11* (2006.01)
   (Continued)

(52) U.S. Cl.
   CPC ........... *A61B 5/1116* (2013.01); *A61B 5/1128* (2013.01); *A61B 5/18* (2013.01);
   (Continued)

(58) Field of Classification Search
   None
   See application file for complete search history.

(56) References Cited

U.S. PATENT DOCUMENTS

| 2011/0112442 A1 | 5/2011 | Meger et al. |
| 2016/0240100 A1 | 8/2016 | Rauhala et al. |
| (Continued) | | |

FOREIGN PATENT DOCUMENTS

| CN | 102113034 A | 6/2011 |
| CN | 202490128 U | 10/2012 |
| (Continued) | | |

*Primary Examiner* — John F Mortell
(74) *Attorney, Agent, or Firm* — Li & Cai Intellectual Property (USA) Office (57) ABSTRACT

A direction control apparatus with a sensor, a method for determining a driver status using the driving control apparatus, and a system for determining the driver status are provided. The direction control apparatus includes at least a pressure sensor to sense a plurality of pressure values applied to multiple positions of the direction control apparatus. When the pressure values are received by a controller of the apparatus, the driver status can be determined according to a change of pressure values over time, or further a change of the positions where pressure is applied. The system can connect with an autopilot system and an alarm system of a vehicle via the controller. Therefore, the system incorporates an autopilot system and issues an alarm when the driver status is determined to be abnormal.

20 Claims, 7 Drawing Sheets

(51) Int. Cl.
  *A61B 5/00* (2006.01)
  *B60W 40/08* (2012.01)
  *B60W 50/14* (2020.01)
  *A61B 5/22* (2006.01)

(52) U.S. Cl.
  CPC .......... *A61B 5/6893* (2013.01); *B60W 40/08* (2013.01); *B60W 50/14* (2013.01); *A61B 5/225* (2013.01); *A61B 2562/0247* (2013.01); *B60W 2040/0872* (2013.01); *B60W 2050/143* (2013.01)

(56) References Cited

U.S. PATENT DOCUMENTS

| | | | |
|---|---|---|---|
| 2017/0101111 A1* | 4/2017 | Fung | B60K 35/00 |
| 2017/0188950 A1 | 7/2017 | Gazdag et al. | |
| 2017/0242506 A1 | 8/2017 | Patel et al. | |
| 2017/0305425 A1* | 10/2017 | Xing | B60W 30/182 |
| 2018/0200598 A1 | 7/2018 | Guan et al. | |

FOREIGN PATENT DOCUMENTS

| | | |
|---|---|---|
| CN | 105549730 A | 5/2016 |
| CN | 105797350 A | 7/2016 |
| CN | 205469242 U | 8/2016 |
| CN | 106027796 A | 10/2016 |
| CN | 106691453 A | 5/2017 |
| CN | 107264612 A | 10/2017 |
| JP | 2008245975 A | 10/2008 |

\* cited by examiner

DIRECTION CONTROL APPARATUS WITH SENSOR, AND METHOD AND SYSTEM FOR DETERMINING DRIVER STATUS USING THE SAME

CROSS-REFERENCE TO RELATED PATENT APPLICATION

This application is a continuation-in-part application of U.S. patent application Ser. No. 15/689,293 filed Aug. 29, 2017, and also claims the benefit of priority to No. 201810884287.7, filed on Aug. 6, 2018 in People's Republic of China. The entire content of the above identified application is incorporated herein by reference.

Some references, which may include patents, patent applications and various publications, may be cited and discussed in the description of this disclosure. The citation and/or discussion of such references is provided merely to clarify the description of the present disclosure and is not an admission that any such reference is "prior art" to the disclosure described herein. All references cited and discussed in this specification are incorporated herein by reference in their entireties and to the same extent as if each reference was individually incorporated by reference.

FIELD OF THE DISCLOSURE

The disclosure is related to a technique for sensing the status of a driver of a vehicle, and in particular to a method for determining driver status using a direction control apparatus with a sensor, and a system thereof.

BACKGROUND OF THE DISCLOSURE

Under strict safety requirements of various vehicles, ships and aircrafts, many safety mechanisms have been developed to ensure travelling safety. Some safety mechanisms are designed specifically for the driver (or pilot). For example, one important topic is to determine if the driver is focused enough on driving.

In one conventional technology, various physiological sensors applied to the driver, such as a sphygmomanometer or a carbon dioxide concentration sensor, are used to monitor the driver's physiological state. The physiological state is such as heartbeat, blood pressure or breathing. A warning message is issued when any abnormality due to fatigue or lethargy is determined.

SUMMARY OF THE DISCLOSURE

In response to the above-referenced technical inadequacies, the present disclosure provides a direction control apparatus with a sensor, and a method and a system for determining driver status.

The present disclosure is related to a direction control apparatus with a sensor. The direction control apparatus can be used to control a moving vehicle such as a car, a plane or a ship. The sensor of the direction control apparatus is used to sense the force generated by a driving action of a driver. The method for determining driver status is used to determine whether or not the driver is in an abnormal state by analyzing the driver's posture. The data sensed by the sensor of the direction control apparatus can be used to monitor the driver status when driving a vehicle. The present disclosure is also related to a system for performing the method.

In an embodiment of the disclosure, the direction control apparatus has a plurality of pressure sensors disposed on the apparatus. The pressure sensors are used to sense a plurality of pressure values at multiple positions over the direction control apparatus. A controller is used to receive the pressure values generated by the pressure sensors. By analyzing the pressure values within a period of time, the driver stats can be determined.

In one aspect of the apparatus, the direction control apparatus is such as a direction control mechanism for controlling direction of the vehicle. The direction control mechanism can be a steering wheel in the form of a structure having the pressure sensors. A change of the pressure values sensed by the pressure sensors of the steering wheel over time can be used to determine the driver status. In an exemplary example, the pressure sensors are attached to a surface of the direction control apparatus.

Further, the pressure values are used to obtain a change in position and a change in number of the positions in the direction control apparatus, and the change of the pressure values can be used to determine the driver status.

In the method for determining the driver status, the pressure sensors of the direction control apparatus periodically sense a plurality of pressure values generated at multiple positions over the direction control apparatus. The change of the pressure values over time can therefore be obtained. The pressure positions with respect to a plurality of pressure values are also obtained. The change of the pressure values over time or the pressure positions thereof are used to determine the driver status.

Further, when determining that the driver status is abnormal, a controller is used to activate an autopilot system, or to alert through an alarm system.

In one further embodiment of the disclosure, in the method, the pressure value with respect to the positions over the direction control apparatus applied by two hands of the driver are obtained. Therefore, the changes at two positions where two pressure values are generated over time can be obtained to determine the driver status therewith. For example, if a change of the pressure values at a first area within a period of time exceeds a first threshold, and simultaneously another change of the pressure values at a second area is lower than a second threshold, it is determined that the statuses of two hands of the driver are different. This condition can be determined as an abnormal status.

In one further aspect, if both changes of the pressure values generated at the first area and the second area within a period of time are determined to be lower than a second threshold, and another pressure value at a third area is also sensed at the same time, it is regarded as abnormal since the condition may indicate that the driver is lying on the direction control apparatus.

In another aspect of the disclosure, if both changes of the pressure values generated at the first area and the second area within a period of time are determined to be lower than the second threshold, it is also regarded as abnormal since the condition may indicate that both hands of the driver are released from the direction control apparatus.

In one aspect of the system for determining driver status, the system can be implemented by a computer system applied to a vehicle. The system includes a pressure sensor disposed on a direction control apparatus, and a controller for performing the method for determining driver status.

These and other aspects of the present disclosure will become apparent from the following description of the embodiment taken in conjunction with the following drawings and their captions, although variations and modifications therein may be affected without departing from the spirit and scope of the novel concepts of the disclosure.

BRIEF DESCRIPTION OF THE DRAWINGS

The present disclosure will become more fully understood from the following detailed description and accompanying drawings.

DETAILED DESCRIPTION OF THE EXEMPLARY EMBODIMENTS

The present disclosure is more particularly described in the following examples that are intended as illustrative only since numerous modifications and variations therein will be apparent to those skilled in the art. Like numbers in the drawings indicate like components throughout the views. As used in the description herein and throughout the claims that follow, unless the context clearly dictates otherwise, the meaning of "a", "an", and "the" includes plural reference, and the meaning of "in" includes "in" and "on". Titles or subtitles can be used herein for the convenience of a reader, which shall have no influence on the scope of the present disclosure.

The terms used herein generally have their ordinary meanings in the art. In the case of conflict, the present document, including any definitions given herein, will prevail. The same thing can be expressed in more than one way. Alternative language and synonyms can be used for any term(s) discussed herein, and no special significance is to be placed upon whether a term is elaborated or discussed herein. A recital of one or more synonyms does not exclude the use of other synonyms. The use of examples anywhere in this specification including examples of any terms is illustrative only, and in no way limits the scope and meaning of the present disclosure or of any exemplified term. Likewise, the present disclosure is not limited to various embodiments given herein. Numbering terms such as "first", "second" or "third" can be used to describe various components, signals or the like, which are for distinguishing one component/signal from another one only, and are not intended to, nor should be construed to impose any substantive limitations on the components, signals or the like.

The disclosure is related to a direction control apparatus with a sensor. The direction control apparatus embodies a control device for driving or piloting a car, a boat or a plane. The control device is such as a steering wheel or a handle stick that is held by two hands of the driver of a vehicle. The sensor of the direction control apparatus is used to sense the driver's posture so as to determine the driver status. The disclosure is also related to a system for determining the driver status. The system can be implemented by a computer system embedded in the vehicle, or a chip that is able to perform a program computation.

Figure 1:
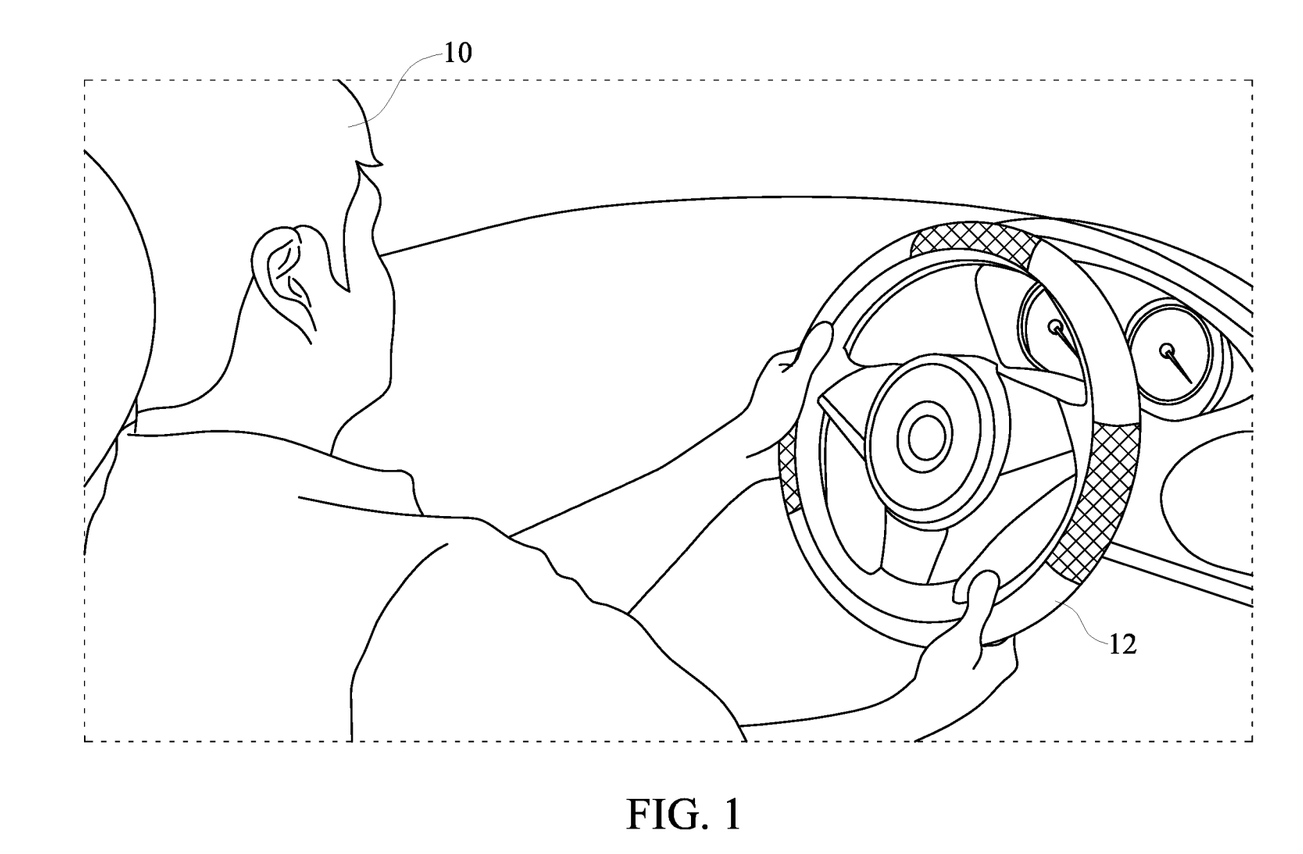
FIG. 1 shows a schematic diagram showing a vehicle adopting a direction control apparatus with a sensor according to one embodiment of the disclosure.

Reference is made to FIG. 1 that schematically depicts a circumstance where a driver of a vehicle operates a direction control apparatus with a sensor in one embodiment of the disclosure.

FIG. 1 shows a driver 10 using two hands to hold a steering wheel 12 in a car. Under a normal driving state, the driver 10 normally holds the steering wheel 12 according to personal habit. When a situation different from the normal driving state occurs, for example, a sudden physiological change in the driver 10, the driver 10 may react to the emergency situation in various possible ways. The method for determining driver status in accordance with the disclosure is to analyze changes of the pressure values read from the sensor of the direction control apparatus. For example, the sensor senses the pressure values from the sensor on the steering wheel 12 when the driver 10 places his/her hands on the steering wheel 12. The changes of the pressure values generated within a period of time can be used to determine the status of the driver 10.

Figure 2:
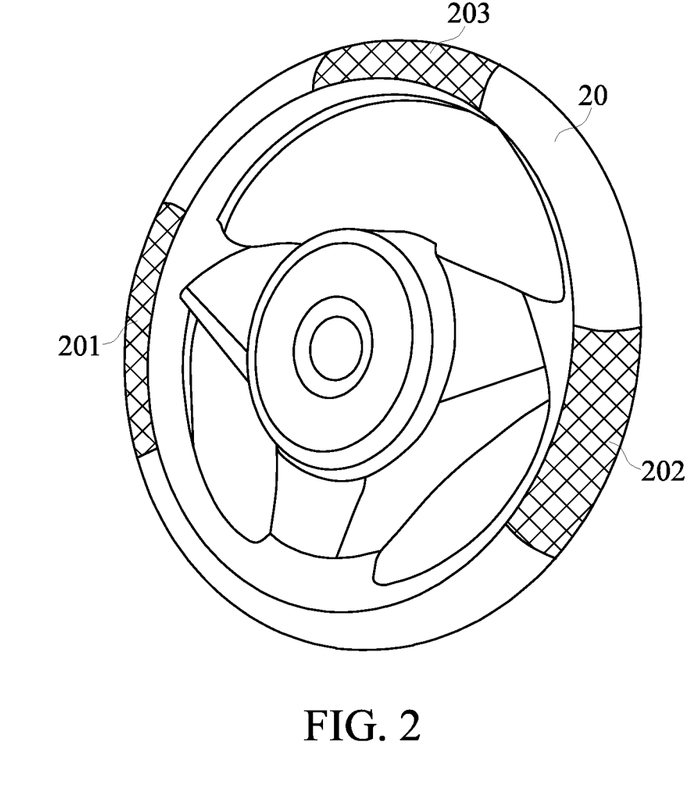
FIG. 2 shows a schematic diagram showing the direction control apparatus with the sensor according to one further embodiment of the disclosure.

FIG. 2 shows a schematic diagram depicting the direction control apparatus with the sensor in one embodiment of the disclosure. A direction control apparatus 20 is shown in the diagram. The direction control apparatus 20 acts as a direction control mechanism such as a steering wheel for a vehicle as exemplarily shown in FIG. 1. The direction control mechanism can be other types or shapes of control devices such as a handle stick or a non-circular steering wheel.

The sensor of the direction control apparatus 20 can be a pressure sensor that is used to sense a plurality of pressure values at multiple positions on the direction control apparatus 20. On the premise that the driver's operation is not affected, the pressure sensor can be a thin-film pressure sensor disposed on a surface of the direction control apparatus 20.

The thin-film pressure sensor can be attached to the positions gripped by the driver's two hands over the direction control apparatus 20. Using the direction control apparatus 20 in the form of a ring structure as an example, the apparatus 20 uses at least three thin-film pressure sensors at at least three positions to perform the method for determining driver status. The three positions are such as a first area 201, a second area 202 and a third area 203. The first area 201 can be an area of the direction control apparatus 20 for placing left hand of the driver under a normal driving state. The second area 202 can be an area of the apparatus 20 for placing right hand of the driver under the normal driving state. Therefore, according to the current example, the first area 201 is an area opposite to the second area 202 over the direction control apparatus 20 in the form of the ring structure. The third area 203 can be an area between the first area 201 and the second area 202.

In an exemplary example, a single thin-film pressure sensor can be used to sense pressure values at multiple positions. The thin-film pressure sensor at the first area 201, the second area 202 or the third area 203 can obtain more than one pressure value at each of the areas. Each area can output one or more pressure values depending on system requirements. When outputting a single pressure value, the thin-film pressure sensor sums up, averages or uses other methods to calculate the pressure values as a single pressure value. For the convenience of explanation, each thin-film pressure sensor is exemplified as outputting only one pressure value in the following embodiments.

In one embodiment, the thin-film pressure sensor can cover more than half or all of the surface area of the direction control apparatus 20. The method is to detect the driver's behavior when he/she operates the direction control apparatus 20.

By the thin-film pressure sensor of the direction control apparatus, changes of the pressure positions where the user's hands grip the direction control apparatus and the pressure values can be obtained. In one embodiment, the changes of the pressure values sensed by the pressure sensor of the steering wheel or the handle stick over time can be obtained. Therefore, the changes can be used to determine the driver's status. In one further embodiment of the disclosure, the driver's status can also be determined by obtaining the changes in the pressure positions and number of the pressure positions.

When considering the cost, instead of the thin-film pressure sensor, it is also possible to apply a board to cover a plurality of single-point pressure sensors that are used for sensing a single-point pressure for taking place of the thin-film pressure sensor. The hard board requires the characteristics of being difficult to be deformed. The hard board allows all the pressure positions over the hard board to be sensed by the pressure sensor under the board so as to generate the pressure values. The size and shape of the hard board are consistent with the surface of the direction control apparatus 20 in order to avoid interfering with the driver operating the direction control apparatus 20. In practice, each of the positions over the direction control apparatus 20 is disposed with the hard board and a corresponding single pressure sensor. The number of the pressure sensors over the direction control apparatus 20 determines the number of pressure positions that can be sensed by the direction control apparatus 20.

Figure 3:
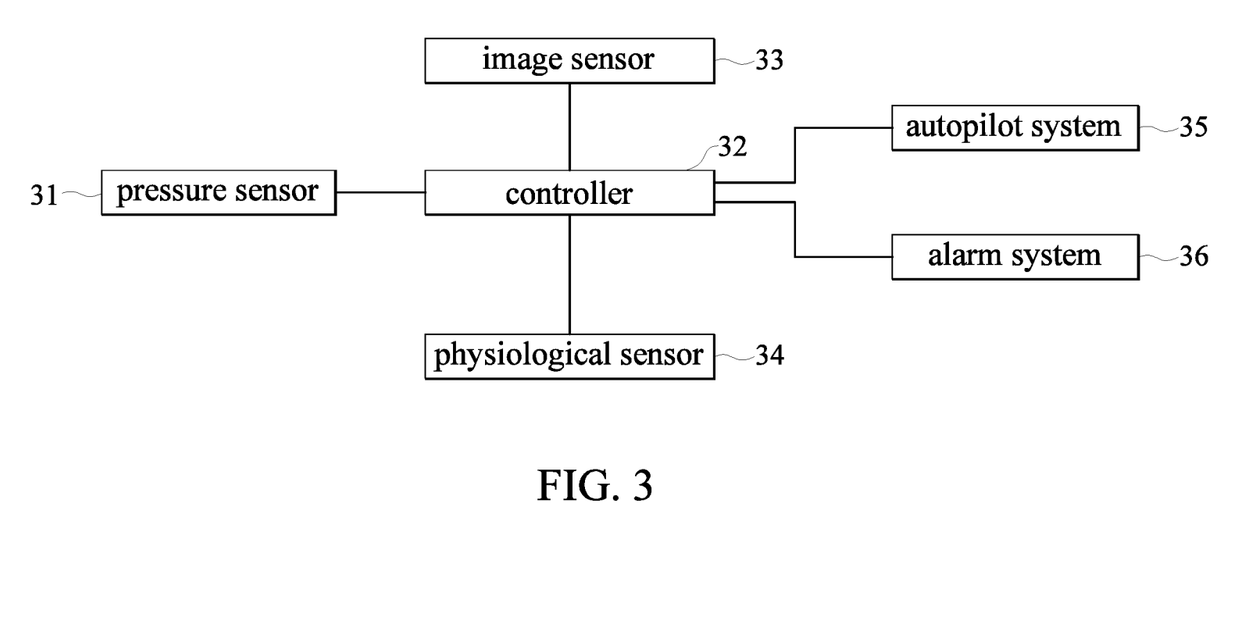
FIG. 3 shows a schematic diagram illustrating a hardware framework of a system for determining driver status in one embodiment of the disclosure.

Reference is made to FIG. 3 that shows a schematic diagram depicting a hardware framework of the system for determining driver status according to one embodiment of the disclosure. The system can be implemented by a computer system that is embedded in a vehicle. The system of the present disclosure is also connected with an original computer system of the vehicle. In one further embodiment, an autopilot system can be provided to intervene in the original driving system of the vehicle.

The system includes a pressure sensor 31 sets on the direction control apparatus. The pressure sensor 31 can be disposed at various positions over the direction control apparatus as needed for sensing the pressure values corresponding to the positions. The direction control apparatus includes a controller 32 that is electrically connected with the pressure sensor 31. The controller 32 is used to receive the pressure values generated by the pressure sensor 31. The controller 32 itself is able to compute these pressure values for performing the method. Alternatively, the system may use an additional processor to determine driver status.

Figure 4:
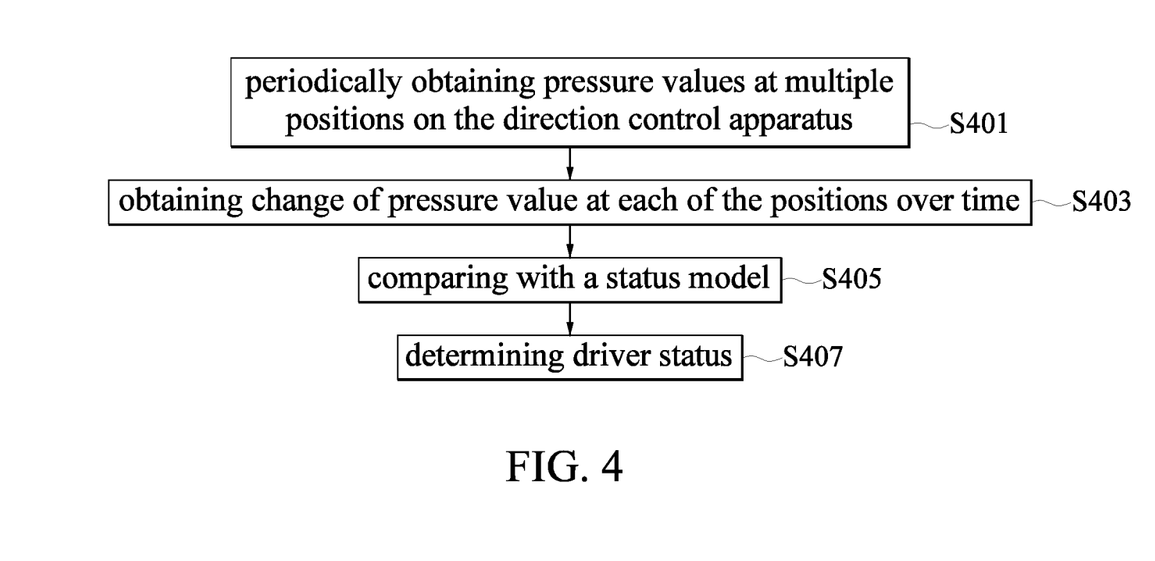
FIG. 4 shows a flow chart describing a method for determining driver status in one embodiment of the disclosure.

Reference is made to FIG. 4 that shows a flow chart of the method for determining driver status. During the driving process, the system for determining driver status is constantly in operation. The system can periodically obtain pressure values at the multiple positions on the direction control apparatus by the pressure sensor (step S401). Through the pressure values calculated at the different positions, any change of the pressure values at each of the positions over time can be obtained (step S403). The system also acquires the pressure positions where the pressure values are generated. After that, in one embodiment, the system predefines a plurality of status models based on a plurality of experiments. The status model records various abnormal statuses of the driver corresponding to different changes of the pressure values at the various positions (or areas) over time. For example, when both two changes of the pressure values (each change means a variation of the pressure values over time) from two pressure sensors (corresponding to two hands of the driver) meet a specific threshold, a first abnormal status of the driver is identified. If another sensor senses another change, the change may correspond to a second abnormal status.

Figure 5:
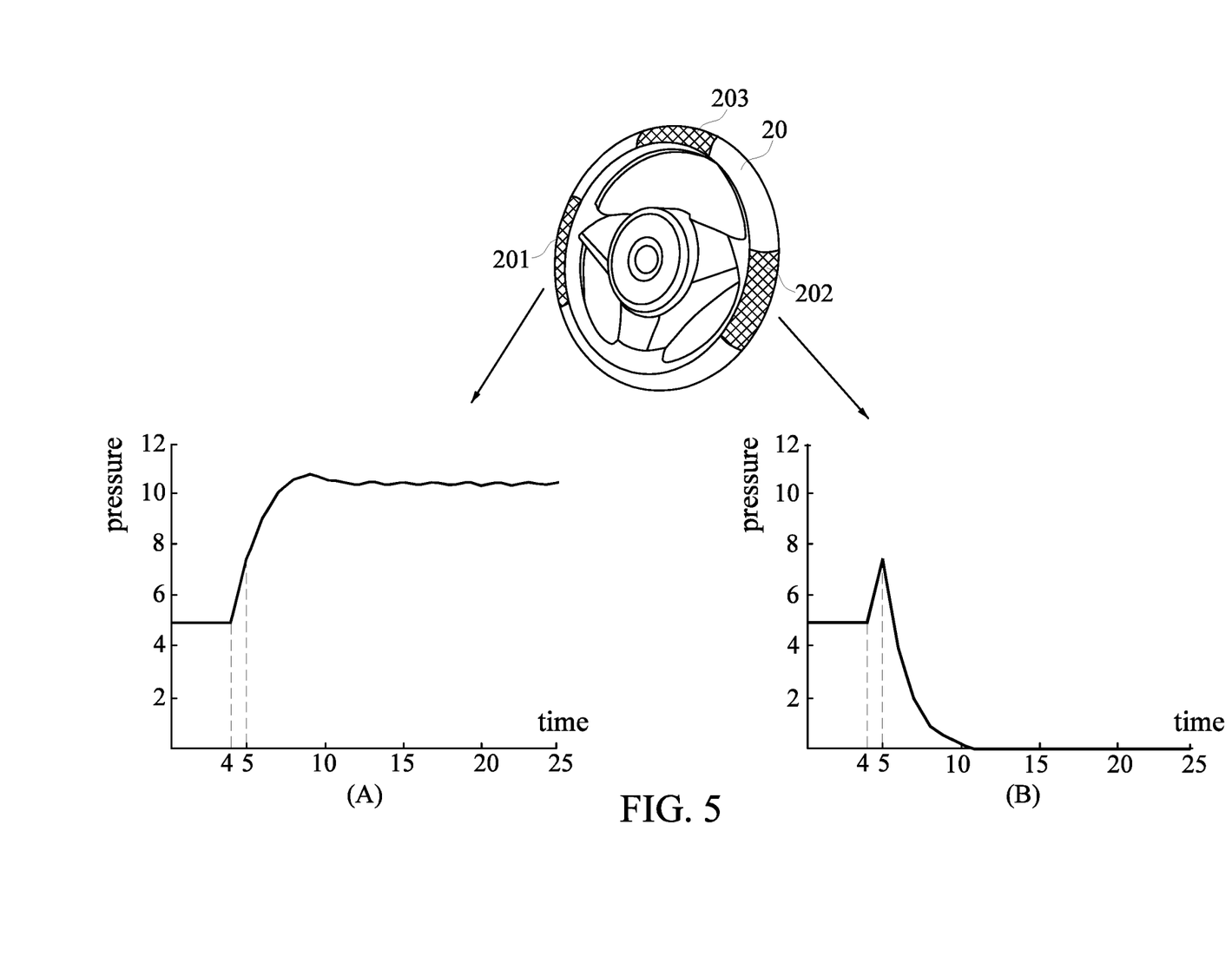
FIG. 5 shows a schematic diagram showing a circumstance relying on changes of sensing values for determining driver status in one embodiment of the disclosure.
Figure 6:
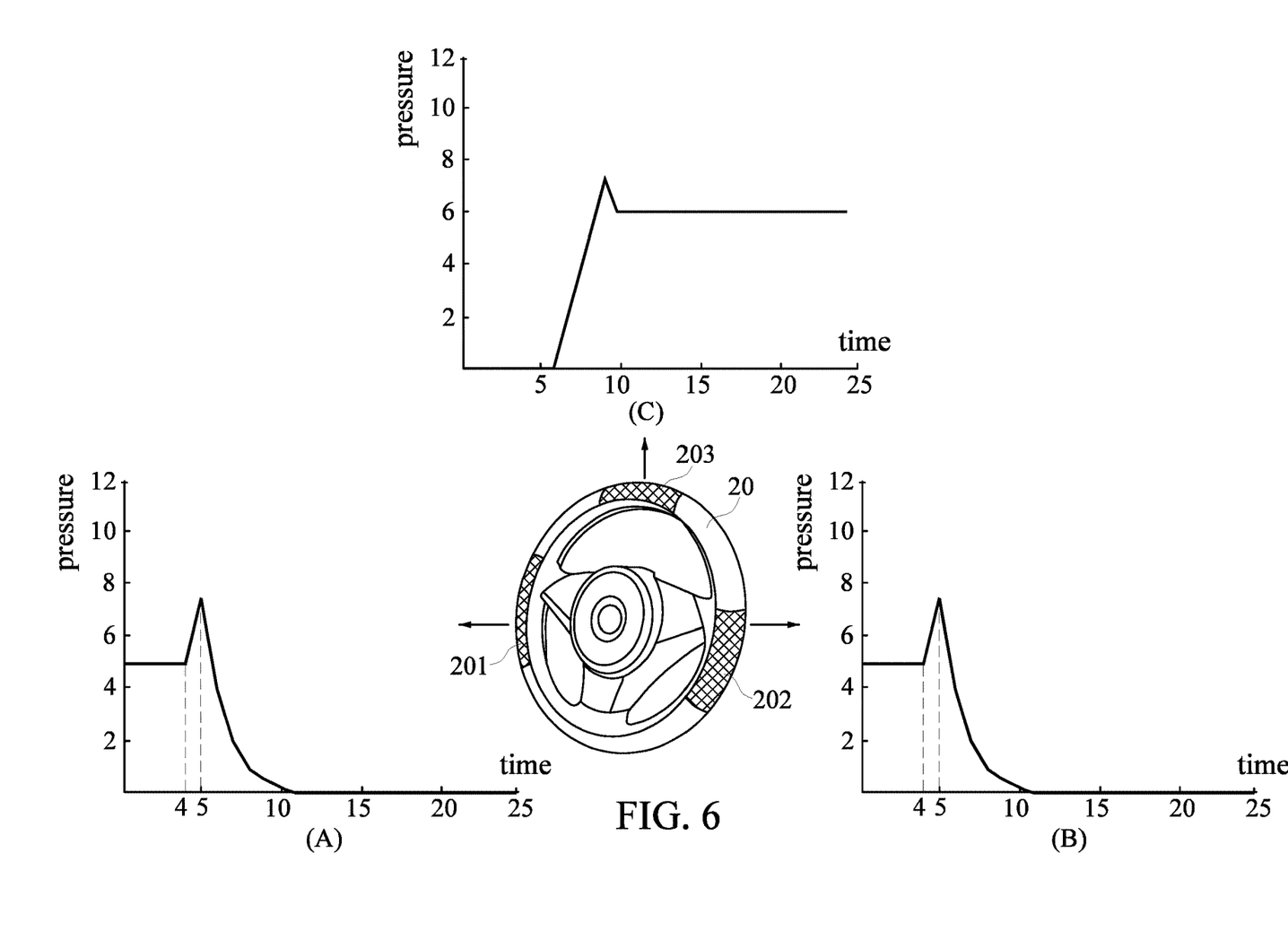
FIG. 6 shows a schematic diagram showing one further circumstance relying on changes of sensing values for determining driver status in one further embodiment of the disclosure.
Figure 7:
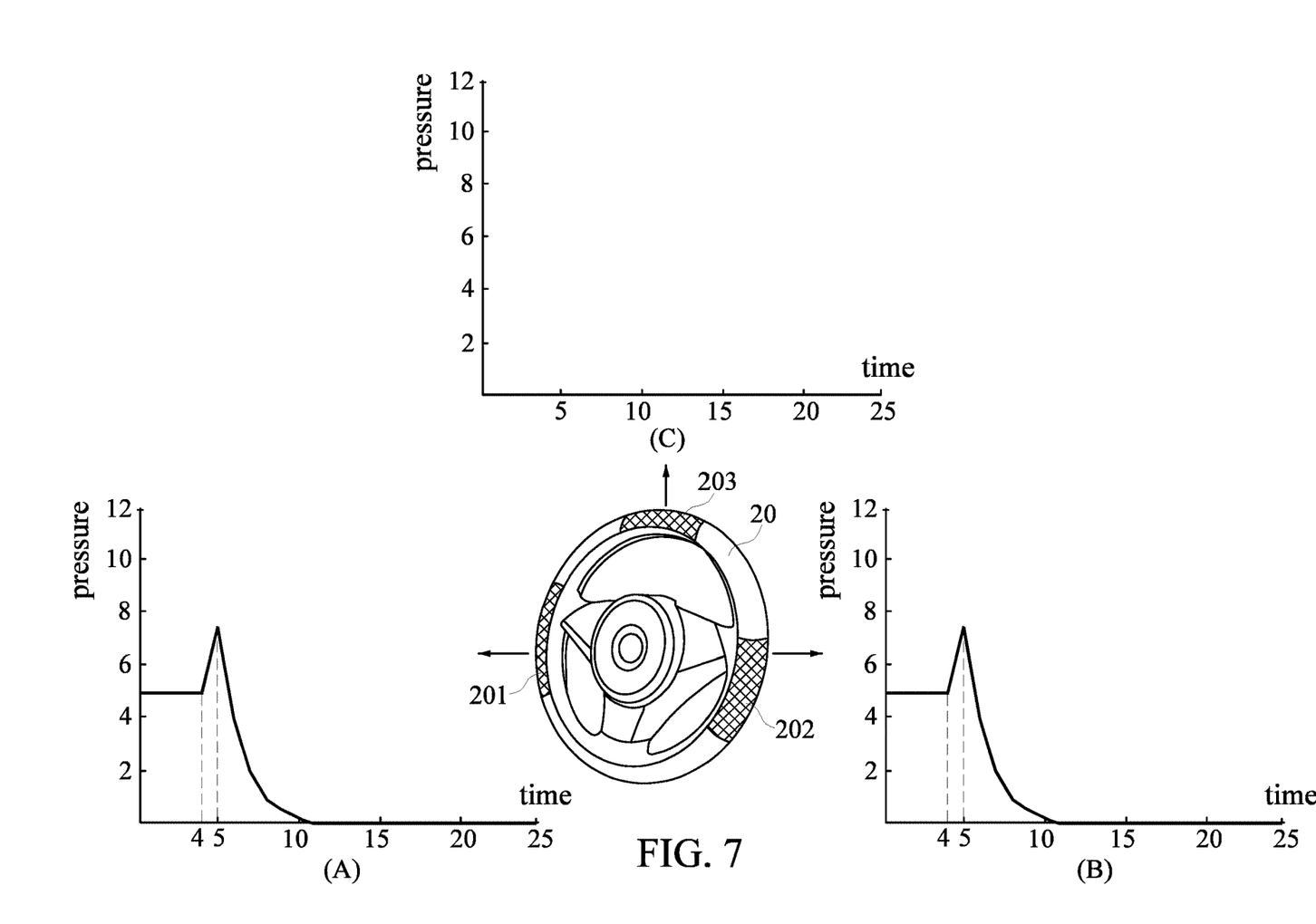
FIG. 7 shows a schematic diagram showing another circumstance relying on changes of sensing values for determining driver status in another embodiment of the disclosure.

FIG. 5 through FIG. 7 show schematic diagrams that depict examples corresponding to the various abnormal statues. The changes of the pressure values allow the system to determine the driver status by continuously reading the pressure values and comparing with the status model (step S405). The driver status can be determined based on the change of the pressure values over time, or a combination of the change of the pressure values over time and corresponding positions (step S407).

When comparing with the status model set up by the system, the changes of the two pressure values can be used to determine the driver status. If at least one of the changes is determined as abnormal, or a number of the pressure positions where the pressure values are generated is determined as abnormal, the controller 32 generates an abnormal signal. In different cases, the abnormal signal could be provided for a follow-up measure.

For example, the system includes an autopilot system 35 that is electrically connected with the controller 32. The autopilot system 35 is activated by the controller 32 while the abnormal signal is received in response to the driver being found abnormal. The autopilot system then takes over the vehicle.

The system also includes an alarm system 36 that is electrically connected with the controller 32. After the abnormal signal is received, the controller 32 drives the alarm system 36 to send a warning message to the driver or an external system.

In a specific embodiment, when the system determines that the driver is in an abnormal status, the system may use other sensors to confirm this abnormal status for avoiding misjudgment. In an exemplary example, if the system finds any abnormal status occurring to the driver, a physiological sensor 34, electrically connected with the controller 32, can be activated to receive physiological signals from the driver for assisting in confirming the driver status.

Furthermore, the system includes an image sensor 33, electrically connected with the controller 32, which can be activated to generate images and perform graphical analysis for assisting in confirming the driver status if any abnormal status is determined. For example, the image sensor 33 can be used to obtain the driver's current posture and facial features for confirming the driver status.

According to the method for determining driver status described above, the pressure values generated by the pressure sensor are the main reference for determining the driver status. The related embodiments are as follows.

FIG. 5 shows a schematic diagram depicting an exemplary circumstance where the driver status can be determined according to the change of the pressure values.

A direction control apparatus 20 is shown in the diagram. Several pressure sensors are disposed at the areas 201, 202 and 203. A curve graph A shown in FIG. 5 represents a pressure curve with respect to a first area 201. The pressure curve shows the change of pressure values corresponding to the driver's left hand gripping the direction control apparatus 20. A curve graph B represents a pressure curve with respect to a second area 202. The pressure curve shows the change of pressure values corresponding to the driver's right hand gripping the direction control apparatus 20.

In an exemplary example, when the driver holds the direction control apparatus 20 with his two hands to drive a vehicle under the normal driving state, the pressure sensors at the first area 201 and the second area 202 of the direction control apparatus 20 sense nearly consistent and stable pressure values. The curves of both the curve graph A and curve graph B have a consistent pressure value before about the 4th second. The curves shown in the curve graph A and the curve graph B show a significant change in pressure values between the 4th second and the 5th second. This significant change in pressure values shows that both the driver's two hands produce obvious actions to increase the pressure within the period of time, and therefore the system determines that the driver is undergoing a violent physiological condition at this time.

Next, the curve graph A shows that the pressure values increase constantly after the 5th second. The curve after the 5th second indicates that the pressure from the driver's left hand applied to the first area 201 of the direction control apparatus 20 increases constantly. After that, the pressure maintains at a certain value, or meets an upper limit of the pressure sensor.

Further, after the 5th second in curve graph B, the pressure values generated at the second area 202 of the direction control apparatus 20 where the driver's right hand grips decline to the lowest level. Specifically, the curves indicative of the pressure values suddenly declines after the 5th second and quickly reaches the lowest level, and the system accordingly determines that the driver's right hand is released from the direction control apparatus 20 after the 5th second. The change of the pressure values over time is able to determine the driver status. In view of FIG. 5, when the driver undergoes the violent physiological condition, for example an angina attack, the severe pain may cause the driver's right hand to release the direction control apparatus 20 and to stroke his heart. The driver's left hand, in the meantime, may apply greater pressure on the direction control apparatus because of the severe pain, or grip the direction control apparatus more tightly for maintaining the traveling direction of the vehicle. The determination makes the system generate a warning signal or activate the autopilot system to take over the vehicle.

The above embodiment shows that the system uses the change of the pressure values at two areas, i.e. the first area 201 and the second area 202, to determine if an abnormal event occurs. Therefore, the driver is determined as abnormal if the system detects that the change of the pressure values generated from the first area 201 within a period of time exceeds a first threshold, e.g. a suddenly increasing value, and the change of the pressure values generated from the second area 202 at the same period of time is lower than a second threshold, e.g. the pressure value reaching the lowest level.

FIG. 6 shows another schematic diagram depicting another exemplary circumstance where the driver status can be determined according to the change of the pressure values.

The pressure sensors are disposed at the areas 201, 202 and 203 of the direction control apparatus 20 as shown in the diagram. A curve graph A represents the change of the pressure values generated at the first area 201 where the driver's left hand grips the direction control apparatus 20. A curve graph B represents the change of pressure values generated at the second area 202 where the driver's right hand grips the direction control apparatus 20. A curve graph C represents the change of pressure values generated at a third area 203 of the direction control apparatus 20. The third area 203 is an area pressed by a part of the driver's body, e.g. head or body, rather than the two hands.

For example, as shown in FIG. 5, the driver uses two hands to hold the direction control apparatus 20 to drive the vehicle. Under the normal driving state, the pressure sensors disposed at the first area 201 and the second area 202 of the direction control apparatus 20 can sense nearly consistent and stable pressure values that are shown as the curve graph A and the curve graph B before the 4th second.

After that, sudden changes of the pressure values are both shown in the curve graph A and the curve graph B between the 4th second and the 5th second. The sudden changes indicate that there is an apparent increase in the pressure applied by the two hands of the driver on the direction control apparatus when a certain condition occurs that may reflect the driver's physiological changes.

Both curves indicative of the pressure values shown in the curve graph A and the curve graph B decline to the lowest level after the 5th second. The changes of the pressure values generated at the two areas over time indicate that the two hands of the driver are released from the direction control apparatus 20 at the 5th second since the pressure values generated at both the first area 201 and the second area 202 around the time suddenly and quickly decline to the lowest level.

Around the 6th second, a pressure value generated by a pressure sensor disposed at the third area 203 over the direction control apparatus 20 is read by the system. The curve indicative of the pressure values at the third area 203 declines after a high level and maintains a pressure value. The changes of the pressure values at the first area 201 and the second area 202 indicate that both hands of the driver are released from the direction control apparatus 20, and the change of the pressure values at the third area 203 indicates an unusual change of the pressure.

Similarly, the method for determining driver status relies on the changes of the pressure values over time to determine the driver's status. According to the embodiment of FIG. 6, the driver undergoes a violent physiological condition at a certain time. For example, a faint condition makes the driver unable to grip the direction control apparatus 20 since both hands may be released from the direction control apparatus 20. The third area 203 may then produce a large pressure value which is then maintained at a certain value. The curve indicative of the pressure values generated at the third area 203 indicates that the driver's head has collided with the direction control apparatus 20 after fainting. This abnormal status causes the system to send a warning message or to activate the autopilot system to take over the vehicle.

According to the above embodiments, the driver is determined as abnormal if the changes of the pressure values generated at the first area 201 and the second area 202 are lower than the second threshold, and the pressure values are then further sensed at the third area 203 at the same time.

FIG. 7 shows one further schematic diagram depicting one further exemplary circumstance where the driver status can be determined according to the change of the pressure values.

The pressure sensors are disposed at the first, second, and third areas 201, 202 and 203 over the direction control apparatus 20. The curve graph A shown in FIG. 7 represents the changes of pressure values generated at the first area 201 where the driver's left hand grips the direction control apparatus 20. The curve graph B represents the changes of pressure values generated at the second area 202 where the driver's right hand grips the direction control apparatus 20. The curve graph C represents the changes of pressure values generated at the third area 203 where one other part of the driver's body, e.g. head or body, contacts the direction control apparatus 20.

In this example, under a normal driving state, the driver uses two hands to grip the direction control apparatus 20 to drive a vehicle with a nearly consistent and stable pressure, during which the pressure values do not change much. Suddenly, both the pressure values generated at the first area 201 and the second area 202 produce the same change of pressure value. The diagram shows that sudden changes of the pressure values shown in the curve graph A and the curve graph B are raised after the 4th second.

The pressure values shown in the curve graph A and the curve graph B are significantly increased between the 4th second and the 5th second. The changes indicate that the driver's two hands apply increased pressure on the direction control apparatus 20 under a certain condition that also reflects the driver's physiological condition. After the 5th second, both the curves shown in the curve graph A and the curve graph B similarly decline to lowest level. This condition indicates that both hands of the driver are released from the direction control apparatus 20 at the same time.

However, under this circumstance, the system fails to read any change of pressure values at the third area 203 of the direction control apparatus 20, or no pressure value is generated at the third area 203. The system determines that no part of the driver's body collides with the direction control apparatus 20 when both hands of the driver are released from the apparatus 20. This condition indicates that the driver's body falls backward when he faints and does not lean forward onto the direction control apparatus 20.

Under this circumstance, the system determines that the driver is fainting according to the changes of the pressure values over time at the areas of the direction control apparatus 20. The system therefore sends a reminding or warning message to the driver, or activates the autopilot system to take over the vehicle.

The system in this aspect firstly considers the changes of the pressure values sensed at the first area 201 and the second area 202. The driver is determined as abnormal when the changes of the pressure values at the first area 201 and the second area 202 are lower than the second threshold at the same time, for example the pressure values reach the lowest level when both hands of the driver are released from the direction control apparatus. The system can then take into account the change of the pressure values sensed at the third area 203 for confirming the abnormal status.

According to above embodiments, the method for determining driver status is performed based on the changes of the pressure values sensed at various positions of the direction control apparatus. Further, the method may incorporate a confirmation procedure, e.g. using a physiological sensor to generate physiological signals or using an image sensor to generate images to be analyzed, for re-confirming the abnormal status. The system can send a warning message to the driver or activate an autopilot system to take over the vehicle when the abnormal status is confirmed.

The foregoing description of the exemplary embodiments of the disclosure has been presented only for the purposes of illustration and description and is not intended to be exhaustive or to limit the disclosure to the precise forms disclosed. Many modifications and variations are possible in light of the above teaching.

The embodiments were chosen and described in order to explain the principles of the disclosure and their practical application so as to enable others skilled in the art to utilize the disclosure and various embodiments and with various modifications as are suited to the particular use contemplated. Alternative embodiments will become apparent to those skilled in the art to which the present disclosure pertains without departing from its spirit and scope.

What is claimed is:

1. A direction control apparatus with a sensor, comprising:
a pressure sensor disposed on a direction control apparatus, used to sense a plurality of pressure values at multiple positions of the direction control apparatus; and
a controller electrically connected with the pressure sensor, used to receive the plurality of pressure values and determine a driver status according to the plurality of pressure values,
wherein the pressure sensor of the direction control apparatus senses pressures on at least a first area and a second area of the direction control apparatus,
wherein the driver status is determined to be abnormal if the pressure values at the first area or the second area significant increase to exceed a first threshold within a first period of time, and then suddenly declining and quickly reaching to a second threshold within a second period of time.

2. The apparatus as recited in claim 1, wherein the direction control apparatus is a direction control mechanism of a vehicle.

3. The apparatus as recited in claim 1, wherein the driver status is determined according to a change of the plurality of pressure values sensed by the pressure sensor disposed on the direction control apparatus at the multiple positions over time.

4. The apparatus as recited in claim 3, wherein the driver status is further determined according to changes of positions where the plurality of pressure values are generated and number of the pressure values.

5. The apparatus as recited in claim 1, wherein the direction control apparatus is in a form of ring structure, the pressure sensor of the direction control apparatus senses pressures on at least the first area, the second area and a third area of the ring structure, wherein the first area is disposed at an opposite side of the second area of the ring structure, and the third area is disposed between the first area and the second area.

6. A method for determining driver status, comprising:
a pressure sensor disposed on a direction control apparatus of a vehicle periodically sensing a plurality of pressure values at multiple positions of the direction control apparatus;
obtaining a change of the plurality of pressure values over time, and obtaining a plurality of positions with respect to the pressure values; and
determining a driver status of the vehicle according to the change of the plurality of pressure values over time, or the positions of the plurality of pressure values, wherein the pressure sensor of the direction control apparatus senses pressures on at least a first area and a second area of the direction control apparatus, wherein the driver status is determined to be abnormal if the pressure values at the first area or the second area significant increase to exceed a first threshold within a first period of time, and then suddenly declining and quickly reaching to a second threshold within a second period of time.

7. The method as recited in claim 6, wherein, if an abnormality occurs in the change of the plurality of pressure values over time, an abnormal signal is generated.

8. The method as recited in claim 7, wherein, one more condition for generating the abnormal signal is that an abnormality occurs in number of the positions of the pressure values.

9. The method as recited in claim 8, wherein, after sensing the pressure values applied to the direction control apparatus held by two hands of the driver at two corresponding positions, changes of the pressure values at the two positions over time are obtained so as to determine the driver status according to the change.

10. The method as recited in claim 9, wherein the two positions include the first area and the second area, the driver status is determined to be abnormal if the pressure values at the first area within a period of time exceeds the first threshold, and the pressure value at the second area within the period of time is changed to be lower than the second threshold.

11. The method as recited in claim 9, wherein the two positions include the first area and the second area, the driver status is determined to be abnormal if both changes of the pressure values generated at the first area and the second area within a period of time are lower than the second threshold, and another pressure value at a third area is sensed at the same time.

12. The method as recited in claim 9, wherein the two positions include the first area and the second area, the driver status is determined to be abnormal if both changes of the pressure values generated at the first area and the second area within a period of time are changed to be lower than the second threshold.

13. The method as recited in claim 6, wherein, when the driver status is determined to be abnormal, a physiological sensor or an image sensor is activated to confirm if the driver is in an abnormal state, a controller is used to activate an autopilot system, and/or a controller is used to notify an alarm system.

14. A system for determining driver status, adapted to a vehicle, comprising:
a pressure sensor disposed on a direction control apparatus, used to sense a plurality of pressure values at multiple positions on the direction control apparatus; and a controller electrically connected with the pressure sensor, receiving the plurality of pressure values and performing a method for determining driver status, wherein the method comprises:

by the pressure sensor, periodically sensing the plurality of pressure values at the multiple positions on the direction control apparatus;

obtaining a change of the plurality of pressure values over time, and obtaining positions with respect to the plurality of pressure values; and determining a driver status according to the change of the plurality of pressure values over time and/or the positions with respect to the pressure values, wherein the pressure sensor of the direction control apparatus senses pressures on at least a first area and a second area of the direction control apparatus, wherein the driver status is determined to be abnormal if the pressure values at the first area or the second area significant increase to exceed a first threshold within a first period of time, and then suddenly declining and quickly reaching to a second threshold within a second period of time.

15. The system as recited in claim 14, wherein an abnormal signal is generated if an abnormality occurs in the change of the plurality of pressure values over time.

16. The system as recited in claim 15, wherein, one more condition for generating the abnormal signal is that an abnormal change occurs in number of the positions.

17. The system as recited in claim 16, wherein two positions corresponding to two hands of the driver include the first area and the second area; the driver status is determined to be abnormal if the pressure values generated at the first area within a period of time are changed to exceeds the first threshold, and the pressure values generated at the second area within the period of time are changed to be lower than the second threshold at the same time.

18. The system as recited in claim 16, wherein two positions corresponding to two hands of the driver include a first area and a second area; the driver is determined to be abnormal if the pressure values generated at the first area and the second area within a period of time are changed to be lower than the second threshold, and another pressure value is sensed at a third area.

19. The system as recited in claim 16, wherein the two positions include the first area and the second area; the driver is determined to be abnormal if the pressure values generated at the first area and the second area within a period of time are changed to be lower than a second threshold.

20. The system as recited in claim 14, wherein, if the driver status is determined as abnormal the controller activates an autopilot system and/or notifies an alarm system that the driver status is determined as abnormal.

* * * * *